United States Patent [19]

Abeler

[11] 4,193,913

[45] Mar. 18, 1980

[54] THERMOPLASTIC VINYL CHLORIDE POLYMERS CONTAINING MONOALKYL-TIN-STABILIZERS

[75] Inventor: Gerd Abeler, Griesheim Über Darmstadt, Fed. Rep. of Germany

[73] Assignee: Ciba-Geigy Corporation, Ardsley, N.Y.

[21] Appl. No.: 881,445

[22] Filed: Feb. 27, 1978

Related U.S. Application Data

[63] Continuation of Ser. No. 806,428, Jun. 16, 1977, abandoned, which is a continuation of Ser. No. 639,146, Dec. 9, 1975, abandoned, which is a continuation-in-part of Ser. No. 540,924, Jan. 14, 1975, abandoned.

[51] Int. Cl.$^2$ .......................... C08K 5/58; C07F 7/22
[52] U.S. Cl. .......................... 260/45.75 S; 260/429.7
[58] Field of Search .................. 260/429.7, 45.75 S; 424/288; 521/121, 126

[56] References Cited

U.S. PATENT DOCUMENTS

| | | | |
|---|---|---|---|
| 2,641,588 | 6/1953 | Leistner et al. | 260/45.75 S |
| 2,648,650 | 8/1953 | Weinkerg | 260/45.75 S |
| 3,390,159 | 6/1968 | Katsumura et al. | 260/45.75 S |
| 3,640,947 | 2/1972 | Gloskey | 260/45.75 S |
| 3,925,309 | 12/1975 | Weisfeld et al. | 260/45.75 S |

FOREIGN PATENT DOCUMENTS 1346999  2/1974  United Kingdom .

OTHER PUBLICATIONS

Journal of Applied Chemistry–vol. 4, Jun. 1954, pp. 314 to 318.
Polyvinyl Chloride–Sarvetnick, 4-1-69, pp. 37 to 48.

Primary Examiner—Veronica P. Hoke
Attorney, Agent, or Firm—Vincent J. Cavalieri

[57] ABSTRACT

Thermoplastic moulding materials for the production of packaging materials for foodstuffs which consist of, or are based on, vinyl chloride polymers and contain monoalkyl-tin-stabilizers.

7 Claims, No Drawings

THERMOPLASTIC VINYL CHLORIDE POLYMERS CONTAINING MONOALKYL-TIN-STABILIZERS

This is a continuation of application Ser. No. 806,428, filed on June 16, 1977, which is a continuation of application Ser. No. 639,146, filed on Dec. 9, 1975. Which is in turn a continuation-in-part of application Ser. No. 540,924, filed on Jan. 14, 1975, all now abandoned.

Monoalkyl-tin tri-thiomercaptocarboxylic acid esters, of which the alkyl radical in the ester group contains 10 to 20 carbon atoms, are excellent heat stabilisers for polymers which consist of, or are based on, vinyl chloride and suitable for the production of packaging materials for foodstuffs because of their low toxicity.

It is known that dialkyl-tin bis-mercaptides, particularly those derived from the mercaptocarboxylic acid esters of fairly short-chain alcohols, are excellent stabilisers for PVC and for numerous copolymers of vinyl chloride. In contrast thereto, the monoalkyl-tin tris-mercaptides as such have attained virtually no significance though they have been proposed simultaneously with the dialkyl-tin bis-mercaptides for the stabilisation of PVC; see, say, U.S. Pat. Nos. 2,641,588 and 2,731,440.

It is also known that the action of the dialkyl-tin sulphur stabilisers can be boosted by admixture of monoalkyl-tin sulphur stabilisers. The optimum effect is generally assumed to be at 20–30% proportion of monoalkyl-tin constituents (see DT-AS 1,669,899 and Informations Chemie No. 119, page 119, April 1973; H. NIEMAN). A further increase in the monoalkyl-tin constituent produces a decrease in the effect, according to the view held hitherto.

It is also known to use butylthiostannonic acid as a stabiliser for PVC moudling materials. However, this stabiliser has a relatively slight effect for its high tin content of 49%. Its pulverulent character furthermore makes it difficult to mix it rapidly into the PVC composition and its pronounced tendency to plate out can in addition lead to difficulties in processing. Alongside dioctyl-tin bis-i-octylthioglycolate, butylthiostannonic acid has not been able to acquire any significant industrial importance. Further, DT-OS 1,924,858 mentions butyl-tin tris-dodecylthioglycolate in one example (see Table IV) as a co-stabiliser together with organic sulphur compounds.

The effectiveness of the known monoalkyl-tin tris-alkylthioglycolates, which contain fairly short-chain alkyl radicals in the esters group, as PVC stabilisers depends to an exceptional degree on the lubricant chosen for the formulation. In most of the lubricant formulations customary at the present time, these stabilisers show a far lower effect than the corresponding dialkyl-tin compounds. This observation applies not only when comparing equal amounts by weight of stabiliser but also when comparing the effect of chemically equivalent amounts. A further very conspicuous fact is that the effectiveness of these monoalkyl-tin stabilisers frequently even worsens as the amount of lubricants added is increased. Undoubtedly, the relatively slight heat-stabilising effect of the previously known monoalkyl-tin stabilisers as compared to the corresponding dialkyl-tin compounds is the cause why the former are, up to the present, of virtually no commercial significance.

It is desirable, particularly from the progressively more important points of view of economy and ecology, to keep the concentration of heavy metals in plastic products as low as possible. Hitherto, the objective of the development of new tin stabilisers was in most cases to bring about an increased effect through increasing the tin content in the stabiliser. As a result, numerous new products were disclosed which admittedly have an increased effect relative to the amount of stabiliser employed but have an effect which is even reduced if viewed with regard to the amount of tin employed. In the light of the above criteria it is more appropriate to relate the effectiveness of the organo-tin stabilisers to the proportion of organically bonded tin (g of tin/100 g of PVC) and not to the amount of stabiliser (g of stabiliser/100 g of PVC).

It is the task of the present invention to develop organo-tin stabilisers which have a better heat-stabilising action in PVC or copolymers based on vinyl chloride than the previously known tin stabilisers and which accordingly make it possible to reduce the amount of tin in the polymer.

Accordingly, the subject of the present invention are thermoplastic moulding materials consisting of, or based on, vinyl chloride polymers, which can optionally contain further metal stabilisers and/or additives, characterised in that they contain, as the stabiliser, per 100 parts by weight of the polymer, 0.2 to 5 parts by weight of a compound of the formula I $$R\text{—}Sn\text{—}(S\text{—}C_nH_{2n}COOR')_3 \qquad (I)$$

in which R is an alkyl radical with 1 to 12 carbon atoms or a vinyl, allyl, phenyl or benzyl radical, R' is an alkyl radical with 10 to 20 carbon atoms and n denotes an integer from 1 to 5, or of mixtures of such compounds. A further subject of the present invention are the compounds of the formula I.

Preferably, the materials contain 0.5 to 2 parts by weight of the organo-tin stabiliser, and preferably, R denotes the methyl, n-butyl or n-octyl radical, R' represents an alkyl radical with 12 to 18, especially 12 to 16, and particularly 12 to 14, carbon atoms, and preferably the $C_nH_{2n}$ radical is a linear alkylene radical, especially with 1 to 2 carbon atoms.

Examples of R which may be mentioned are: ethyl, propyl, i-butyl, i-pentyl, hexyl, 2-ethylhexyl, nonyl, decyl, 2-methylnonyl and lauryl. Examples of R' are: decyl, stearyl, eicosyl, i-tridecyl, i-hexadecyl and i-octadecyl, but especially dodecyl, tetradecyl and hexadecyl, as well as the commercially available mixtures of alcohols known as alfols which substantially have alkyl groups with the same number of carbon atoms and are predominantly branched. The alkyl groups are here described as "alfyl", the number of C atoms being shown behind the name, in parentheses.

Mixtures of the compounds of the formula I with on another, mixtures in equal amount, preferably with up to 50% of the analogous dialkyl-tin compounds, relative to the amount of the stabiliser of the formula I, and/or mixtures with other metal stabilisers, can also be used for the moulding materials according to the invention. Amongst the other metal stabilisers, those based on organo-tin are preferred. They are employed at most in equal amount, preferably in amounts of up to 50%, relative to the amount of the stabiliser of the formula I. In addition, metal stabilisers, for example stabiliser systems containing calcium/zinc or barium/cadmium, should be mentioned in this context.

The stabilisers for the moulding materials according to the invention are manufactured according to known processes, especially by the reaction of stannonic acids or monalkyl-tin oxides with mercaptocarboxylic acid esters, or by reaction of alkyl-tin trichlorides with the mercaptocarboxylic acid esters, in the presence of HCl acceptors.

Examples of mercaptocarboxylic acid esters to be employed are: thioglycollic acid cetyl ester, thioglycollic acid tetradecyl ester, thioglycollic acid dodecyl ester, thioglycollic acid tridecyl ester, 2-mercaptopropionic acid n-octadecyl ester, β-mercaptopropionic acid i-octadecyl ester, thiolactic acid lauryl ester, β-mercaptobutyric acid tetradecyl ester, 4-mercaptobutyric acid eicosyl ester and 5-mercaptovaleric acid pentadecyl ester.

Vinyl chloride polymers or vinyl chloride copolymers are used for the moulding materials according to the invention. Suspension polymers and bulk polymers, and emulsion polymers which have been washed and thus of low emulsifier content are preferred. Examples of comonomers for the copolymers are: vinylidene chloride, trans-dichloroethylene, ethylene, propylene, butylene, maleic acid, acrylic acid, fumaric acid and itaconic acid.

The moulding materials according to the invention are manufactured in accordance with known processes by incorporating the stabiliser and, optionally, additional stabiliser into the polymer. A homogeneous mixture of stabiliser and PVC can be produced, for example, with the aid of a twin-roll mixer at 150°-210° C. Depending on the end use of the moulding material, further additives, such as lubricants, preferably montan waxes or glycerol esters, plasticisers, fillers, modifiers, such as, say, additives for improving the impact strength, pigments and/or light stabilisers can also be incorporated before, or simultaneously with, the incorporation of the stabiliser.

The moulding materials according to the invention can be converted into shaped articles in accordance with the shaping processes customary for the purpose, for example by extrusion, injection moulding or calendering. They can be used particularly advantageously for the manufacture of packaging materials for foodstuffs especially films. For this end use, additionally incorporated stabilisers and/or other additives must of course be physiologically harmless.

Compared to known organo-tin compounds according to the state of the art, the monoalkyl-tin compounds of the formula I have a better heat-stabilising action. This finding is surprising and unforeseeable because the introduction of longer radicals into the ester group of the monoalkyl-tin tris-thiocarboxylic acid ester reduces the tin content and hence the concentration of the actual active group. Furthermore, it is surprising and particularly advantageous that through the choice of certain long-chain alkyl radicals in the ester group the unfavourable dependence on the lubricant, which has already been mentioned, can be eliminated and that the activity of the stabilisers, to be employed according to the invention, in the customary lubricant formulations even exceeds that of the most effective dialkyl-tin stabilisers, including those mixed with monoalkyl-tin stabilisers.

A further advantage of the stabilisers to be employed according to the invention is that where necessary they provide the possibility of processing tin-stabilised vinyl chloride polymers containing plasticiser to give physiologically harmless finished articles, since their toxicity is in certain cases even lower than that of the physiologically harmless di-n-octyl-tin stabilisers.

The examples which follow explain the invention in more detail. The percentages given therein are % by weight.

(A) MANUFACTURE OF THE STARTING MATERIALS

EXAMPLE 1: Manufacture of methyl-tin tris-(myristyl-thioglycollate)

12.0 g of methyl-tin trichloride are reacted in accordance with known processes with 43.9 g of thioglycollic acid myristyl ester in the presence of 15 g of sodium bicarbonate. After completion of the reaction, the reaction product is freed from the precipitate by filtration, and dried. The product is a colourless, oily liquid.

Found % Sn 11.5 (calculated 11.9). Found % S 9.9 (calculated 9.7).

EXAMPLE 2: Manufacture of butyl-tin tris-(lauryl-thioglycollate)

A mixture of 10.4 g of butylstannonic acid and 39.1 g of thioglycollic acid lauryl ester is heated for 45 minutes in a vacuum of 10 mm Hg to 100° C., whilst withdrawing the water of reaction produced. After filtration, a water-clear oily liquid is obtained as the reaction product.

Found % Sn 12.1 (calculated 12.4). Found % S 9.8 (calculated 10.0).

EXAMPLE 3: Manufacture of butyl-tin tris-(cetyl-thioglycollate)

10.4 g of butylstannonic acid are reacted with 47.5 g of thioglycollic acid cetyl ester as in Example 3. The reaction product obtained is a colourless viscous liquid which gradually solidifies to a wax below room temperature.

Found % Sn 10.2 (calculated 10.4). Found % S 8.4 (calculated 8.6).

EXAMPLE 4: Manufacture of butyl-tin tris(alfyl(12)-thioglycollate) containing some dibutyl-tin compound (a) 129.5 g of thioglycollic acid and 262.5 g of Alfol 12 ®are esterified in benzene in the presence of p-toluenesulphonic acid as the catalyst. After completion of the reaction, the mixture is repeatedly washed with sodium bicarbonate solution and water, and dried. After distilling off the solvent, an oil liquid remains, which solidifies to a wax after prolonged standing. The SH content of the ester is 11.5%.

(b) 95.8 g of a mixture of 84% of butylstannoic acid and 16% of dibutyl-tin oxide are heated with 353 g of the ester obtained according to (a) to 100° C. in vacuo for 45 minutes. The reaction product obtained after filtration is a colourless liquid.

Found % Sn 11.3 (calculated 11.8). Found % S 9.4 (calculated 9.2).

EXAMPLE 5: Manufacture of butyl:tin tris(alfyl(14)-thioglycollate) containing some dibutyl-tin compound.

As the first stage, thioglycollic acid alfyl(14) ester is manufactured in accordance with the same process as in Example 5(a). The ester is a waxy, low-melting substance with an SH content of 10.0%. 85 g of the ester are reacted with an oxide mixture of 84% of butylstannonic acid and 16% of dibutyl-tin oxide, as in Example 5(b). The reaction product is a colourless, oily liquid.

Found % Sn 10.6 (calculated 10.5). Found % S 8.4 (calculated 8.1).

EXAMPLE 6: Manufacture of butyl-tin tris-(stearyl thioglycollate)

160 g of thioglycollic acid stearyl ester, with an SH content of 8.3%, are reacted with 27.6 g of monobutyl-tin oxide analogously to Example 3. The reaction product is waxy and has a melting point of 42° C.

Found % Sn 10.1 (calculated 9.9). Found % S 7.8 (calculated 8.3).

EXAMPLE 7: Manufacture of butyl-tin tris(i-tridecyl thioglycollate) containing some dibutyl-tin compound As the first stage, 200 g of i-tridecanol and 92 g of thioglycollic acid are reacted, like in Example 5(a), to give thioglycollic acid i-tridecyl ester. Determination of the SH content gives a value of 10.8%.

68.4 g of a mixture of 84% of butylstannonic acid and 16% of dibutyl-tin oxide are then reacted, as in Example 5(b), with 268.3 g of the ester. The reaction product is a light yellow liquid.

Found % Sn 10.8 (calculated 11.2). Found % S 9.0 (calculated 8.7).

EXAMPLE 8: Manufacture of butyl-tin tris-(i-octadecyl thioglycollate)

i-Octadecanol of technical degree of purity, and thioglycollic acid, are reacted, like in Example 5a), to give i-octadecyl thioglycollate, of SH content 8.4%. 300 g of the ester are reacted with 55.5 g of butylstannonic acid, like in Example 5(b). The resulting product is light yellow and viscous.

Found % Sn 8.9 (calculated 8.8). Found % S 7.9 (calculated 7.1).

EXAMPLE 9: Manufacture of octyl-tin tris(alfyl(14)-thioglycollate) containing some dioctyl-tin compound 14.9 g of a mixture of 91% of octyl-tin oxide and 9% of dioctyl-tin oxide are reacted, like in Example 3, with 50.0 g of thioglycollic acid alfyl(14) ester. The reaction product is a light yellow liquid.

Found % Sn 10.2 (calculated 9.8). Found % S 8.0 (calculated 7.8).

EXAMPLE 10: Manufacture of octyl-tin tris-(cetyl-thioglycollate) containing some dioctyl-tin compound 35.4 g of a mixture of 91% of monooctyl-tin oxide and 9% of dioctyl-tin oxide are reacted with 121 g of thioglycollic acid cetyl ester, like in Example 11. The reaction product is a colourless, oily liquid.

Found % Sn 9.6 (calculated 10.2). Found % S 7.8 (calculated 8.1).

(B) USE EXAMPLES

EXAMPLE 11: Heat stability test

A dry blend, consisting of 100 parts of suspension PVC, 0.5 part of montan wax, 1.0 part of monoglycerol ester and 1.0 part of organo-tin stabiliser according to the table below, is milled on a laboratory mill at 190° C. Every 5 minutes, an 0.3 mm thick piece of film is taken off to asist the discolouration. The time in minutes after which the milled film shows a recognisable colour change to light brown-yellow is quoted as a measure of the heat stability.

| Experiment No. | Stabiliser | Heat stability of the moulding material (minutes) |
| --- | --- | --- |
| 1 | $CH_3Sn(SCH_2COO-C_{14}H_{29})_3$ corresponds to Example 1 | 25 |
| 2 | $C_4H_9Sn(SCH_2COO\text{-alfyl }14)_3$ corresponds to Example 5 | 25 |
| 3 | $C_8H_{17}Sn(SCH_2COO\text{-n-}C_{16}H_{33})_3$ corresponds to Example 10 | 25 |

The moulding materials according to the invention (Experiments 1, 2 and 3) accordingly have a very good heat stability.

EXAMPLE 12

Moulding materials consisting of 100 parts of bulk-polymerised PVC and 0.3 part of montan wax together with the organo-tin stabilisers according to the table which follows are examined for their heat stability, analogously to Example 11. The amounts of stabiliser are calculated to correspond to the use of 0.15 g of Sn/100 g of PVC.

| Experiment No. | Stabiliser Product from Example No. | Amount of stabiliser used | Time in minutes for which the films remain colourless |
| --- | --- | --- | --- |
| 1 | 2 | 1.24 | 25 |
| 2 | 3 | 1.47 | 35 |
| 3 | 4 | 1.33 | 30 |
| 4 | 8 | 1.69 | 30 |
| 5 | 9 | 1.47 | 35 |

A repetition of the experiment with suspension PVC gives the same result.

EXAMPLE 13

100 parts of a vinyl chloride/vinyl acetate copolymer (vinyl acetate content 10%, K-value 60 to 61) are premixed with 0.5 part of montan wax, 1.0 part of monoglycerol ester and an organo-tin stabiliser of the formula $C_8H_{17}Sn(SCH_2COO\text{-n-}C_{16}H_{33})_3$. The amount of organo-tin stabiliser (1.35 g) is so chosen that 0.13 g of tin are present per 100 parts of copolymer. After milling for 20 minutes at 180° C., only very slight yellowing is detectable.

EXAMPLE 14

A mixture of 100 parts by weight of suspension PVC (K-value 71), 40 parts by weight of di-2-ethylhexyl phthalate, 0.3 part by weight of montan wax and 0.5 part by weight of octyl-tin tris-cetyl-thioglycollate, corresponding to 0.05 g of Sn/100 g of PVC, is milled on a laboratory mill at 180° C. until yellowing beings to occur.

The time for which the mixture is milled until a very slight yellowing is just detectable is 74 minutes. After 105 minutes, the mill hide is slightly yellow.

EXAMPLE 15

Experiment 1: A dry blend, consisting of 100 parts by weight of suspension PVC (K-value 58), 1.0 part by weight of wax ester and 0.2 part by weight of montan wax as the lubricant, 1.0 part by weight of acrylic resin as a processing aid, 12.0 parts by weight of MBS modifying resin, as an additive to improve impact strength, and 0.8 part by weight of methyl-tin tris-(myristyl-thioglycollate), corresponding to 0.09 part of tin, is milled on a laboratory mill at 190° C. Every 5 minutes, an 0.3 mm thick piece of film is removed to assess the discolouration.

The milling time to reach a very slight yellow discolouration is 15 minutes and to reach a light yellow discolouration is 20 minutes.

Experiment 2: The above experiment is repeated with 1.1 parts by weight of the same stabiliser, corresponding to 0.13 part of tin. The very slight yellow discolouration in this case occurs after 20 minutes, and the light yellow discolouration after 25 minutes.

(C) TOXICOLOGICAL TESTING
EXAMPLE 16

Testing of

| | | |
|---|---|---|
| (I) | $(n\text{-}C_8H_{17})_2Sn(SCH_2COO\text{-}i\text{-}C_8H_{17})_2$ | comparison |
| (II) | $n\text{-}C_8H_{17}Sn(SCH_2COO\text{-}i\text{-}C_8H_{17})_3$ | |
| (III) | $n\text{-}C_8H_{17}Sn(SCH_2COO\text{-}n\text{-}C_{14}H_{29})_3$ | |

(a) Acute oral $LD_{50}$

Compound III was weighed into an Erlenmeyer flask. It was diluted at 30 and 50% with carboxymethylcellulose and administered by oral intubation.

The compound was tested on 40 rats (20 males/20 females). They were 6 to 7 weeks old and weighed 160 to 180 g.

The males and females were segregated and housed in Macrolon cages in groups of 5 in a room kept at a constant temperature of 22 ±1° C. and a relative humidity of approximately 50%. They received water and food ad libitum. The rats were starved during one night before starting the treatment. The doses were 3170, 4640, 6000 and 10,000 mg/kg body weight. No animal died over a period of 14 days at all concentrations. In the autopsy of killed animals no substance related gross organ changes were seen.

The acute oral $LD_{50}$ of compound III in rats of both sexes observed over a period of 14 days is therefore greater than 10,000 mg/kg. The compound has therefore a slight acute toxicity to the rat by this route of administration.

As a comparison the acute oral $LD_{50}$ of compound I is only 2000 mg/kg and that of compound II only 5000 mg/kg (b) Noeffect-level Compound III was administered in the diet to groups of 30 (groups 2 and 3) and 40 (group 4) rats at concentrations of 300, 1000 and 3000 ppm respectively (equivalent to an average daily intake of 19, 62 and 179 mg/kg body weight), for not less than 90 days. Forty rats in the control group received the same diet but without the addition of Compound III.

No deaths occured and no clinical symptoms were recorded.

Male rats treated with 3000 ppm following day 14 gained less body weight than untreated controls. At termination of treatment the body weights of these rats were slightly below those from untreated control animals. This marginal decrease of body weight gain went parallel with a decreased feed consumption of top dose rats, further demonstrating that it resulted from reduced feed uptake and was related to poor palatability of the diet compound mixture.

Ten rats (5+5) from each of groups 1 (control) and 4 (3000 ppm) were retained without treatment for 28 days after the end of the main study, as a recovery experiment.

In group 4 there was no significant difference between these groups in respect of body weight gains, for consumption, laboratory parameters or organ weight data. No histopathological changes were seen in group 4 rats after the recovery period.

The no effect level is 3000 ppm (equivalent to an average daily intake of 179 mg/kg body weight of compound III). As a comparison compound I shows a no effect level of only 25 ppm and compound II of only 500.

These unobvious results demonstrates the superiority of the claimed tin stabilizers in the use for packaging materials for foodstuffs.

What we claim is:

1. A compound of the formula $$R-Sn-(S-CH_2COO-n-C_{14}H_{29})_3$$

wherein R is methyl, n-butyl or n-octyl.

2. The compound according to claim 1 having the formula $(n-C_8H_{17})Sn(SCH_2COO-n-C_{14}H_{29})_3$.

3. The compound according to claim 1 having the formula $(n-C_4H_9)Sn(SCH_2COO-n-C_{14}H_{29})_3$.

4. The compound according to claim 1 having the formula $CH_3Sn(SCH_2COO-n-C_{14}H_{29})_3$.

5. A thermoplastic moulding material consisting essentially of a vinyl chloride polymer, stabilized with 0.2 to 5 parts by weight per 100 parts of the polymer of the compound of claim 1.

6. The moulding material according to claim 5, characterized in that the polymer is a suspension, bulk or emulsion polymer of low emulsifier content.

7. The moulding material according to claim 5, characterized in that it contains 0.5 to 2 parts by weight of the stabilizer of the formula $(n-C_8H_{17})Sn(SCH_2COO-n-C_{14}H_{29})_3$.

* * * * *